United States Patent [19]

Richecoeur et al.

[11] Patent Number: 5,213,763
[45] Date of Patent: May 25, 1993

[54] DEVICE AND METHOD FOR TRANSFERRING A FLUID SAMPLE BETWEEN TWO CHAMBERS AND APPLICATION IN PARTICULAR TO GAS CHROMATOGRAPHY

[75] Inventors: Alain Richecoeur, Rueil Malmaison; Annick Pucci, Croissy sur Seine; Joseph Larue, Chambourcy; José Sanchez, Saint Martin du Tertre, all of France

[73] Assignee: Institut Francais du Petrole, Rueil-Malmaison, France

[21] Appl. No.: 594,978

[22] Filed: Oct. 10, 1990

[30] Foreign Application Priority Data

Oct. 10, 1989 [FR] France .................................. 89 13262

[51] Int. Cl.⁵ ............................................. G01N 1/10
[52] U.S. Cl. ................................. 422/100; 73/863.71; 73/863.81; 422/63; 422/103; 436/179; 436/180; 436/174
[58] Field of Search .................... 422/63, 70, 100, 101, 422/81, 82, 103; 436/180, 53, 179, 161, 174; 73/863.71, 863.73, 863.82, 863.81

[56] References Cited

U.S. PATENT DOCUMENTS

| | | | |
|---|---|---|---|
| 3,990,853 | 11/1976 | Godin | 422/82 X |
| 3,991,055 | 11/1976 | Godin et al. | 23/259 |
| 4,152,391 | 5/1979 | Cabrera | 422/103 |
| 4,234,543 | 11/1980 | Matovich | 422/109 |
| 4,476,733 | 10/1984 | Chlosta et al. | 73/863.91 |
| 4,534,941 | 8/1985 | Stephens et al. | 422/70 |
| 4,576,706 | 3/1986 | Takata et al. | 204/409 |
| 4,641,541 | 2/1987 | Sharp | 73/864.81 |
| 4,805,469 | 2/1989 | Commarmot | 73/864.81 |
| 4,933,146 | 6/1990 | Meyer et al. | 422/63 |
| 4,957,706 | 9/1990 | Ramette et al. | 422/100 |

Primary Examiner—James C. Housel
Assistant Examiner—Long V. Le
Attorney, Agent, or Firm—Antonelli, Terry, Stout & Kraus

[57] ABSTRACT

A method for transferring a fluid sample from a first chamber to a second chamber separated from the first chamber involves opening a closed cavity defined between the end portions of two coaxially arranged cylindrical rods while in the first chamber, then closing the open cavity in the first chamber to enclose the fluid sample, transferring the closed cavity from the first chamber to the second chamber by effecting axial movement of the rods relative to the chambers, then opening the closed cavity in the second chamber to allow the fluid sample to enter the second chamber. A device for carrying out this method is provided with first and second rods arranged to move along a common axis, the device including an arrangement for effecting displacement of the rods relative to each other and relative to the chambers or displacement of the rods together while the end portions of the rods are in contact to effect transfer of the fluid sample from one chamber to the other.

15 Claims, 2 Drawing Sheets

DEVICE AND METHOD FOR TRANSFERRING A FLUID SAMPLE BETWEEN TWO CHAMBERS AND APPLICATION IN PARTICULAR TO GAS CHROMATOGRAPHY

BACKGROUND OF THE INVENTION

The present invention relates to a method and device for transferring a fluid sample from a first chamber to a second chamber. The invention also applies to taking a microvolume sample in thermodynamic equilibrium from a chamber and transferring this sample in a pipe.

In particular, the invention relates to sampling a fluid flowing in a pipe at a very low temperature ($-20°$ C. to $-100°$ C.) and high pressure (about 100 bars) and transferring the sample to a line at high temperature ($250°$ C. for example) and low pressure, such as a gas chromatography line.

The invention allows the composition of a fluid flowing in a system to be determined without substantially altering the volume of fluid sampled.

In fact, the difficulty of in-line sampling of a liquid in equilibrium with a gas phase, hence at its bubble point, resides in the fact that the sample must be trapped under strict conditions of thermodynamic equilibrium, then entirely vaporized by heating and/or expansion in the chromatography carrier gas.

SUMMARY OF THE INVENTION

The invention offers a device for transferring a fluid sample from a first chamber to a second chamber separated from the first chamber.

This device is characterized in particular by comprising a set of a first rod and a second rod, each rod having a lengthwise shaft axis, the lengthwise axes of these rods being coaxially arranged, at least the first rod having one end or end portion that has a cavity formed therein, the cavity then being open, the end portion being arranged to cooperate with an end portion of the second rod to form a closed cavity when the two end portions are in contact, the first and the second rods each having an outer cylindrical wall with the same dimensions, the cylindrical wall of the first rod and the cylindrical wall of the second rod being designed to cooperate with a central circumferential sealing element providing a seal between the first chamber and the second chamber, along the common axis of said rods, means for displacing said rods along the common axis relative to the chambers, designed to move the closed cavity between the first and second chambers, opening means allowing said closed cavity to be opened in the first and second chambers, and closing means allowing an open cavity to be closed when the sample is transferred from the first chamber to the second chamber.

The first and second rods may pass right through the first and the second chamber and cooperate respectively with a first or a second lateral sealing element ensuring, along the first or second of the rods, confinement of the first or second chamber respectively.

The second chamber may communicate with an analysis device.

The second chamber may be located in a sampling line in which a carrier fluid flows.

When one of said chambers has to be heated with respect to another of said chambers, said chamber may be located in an electrically conductive line and be traversed by a fluid, the device may have electrical means designed to cause a current to flow in said line in order to produce, by the Joule effect, heating of said line and the central sealing element, and one of said rods located in said chamber will be electrically resistive.

When at least one of said chambers must be cooled or heated and kept at a given temperature, this chamber may be located in a line in which a fluid flows; the line may contain a coil around said chamber so that the flow of fluid cools or heats said chamber.

Said line may have, at least outside one of said chambers, heat-exchange means external to said line that are designed for the transfer of heat energy between said line and a medium external to said line.

Said line may have a coil around the chamber to be heated or cooled, and the heat-exchange means may be disposed in said line outside said coil.

At least one of said sealing elements may be made of a polymer material of the polyimide type.

The first and the second rods may pass right through the first and second chambers, and cooperate with a first and a second lateral sealing element respectively ensuring, at the locations of the first and second rods respectively, confinement of the first and the second chambers respectively, the device having a shaft integral with said first and second chambers, with the central sealing element, with the first and second lateral sealing elements, a first and a second stop which are integral with the first and second rods, said shaft moving relative to said rods between said stops in order to place the ends of the first and second rods in the first chamber when the shaft is in contact with the first stop as well as in the second chamber when the shaft is in contact with the second stop, and the means for opening said cavity may include elastic elements allowing displacement of the stops under the action of a given force produced by said shaft, in order to bring about the opening of said cavity, as well as allowing replacement of the stops when said given force is removed, in order to cause said cavity to close, the ends of the first and second rods being in contact.

The first or second rods may be made of a ceramic material.

The invention also proposes a method for transferring a fluid sample from a first chamber to a second chamber separated from the first chamber. This method is characterized in particular by the following successive stages:

a cavity defined by the ends of two coaxial cylindrical rods having cylindrical walls of the same dimensions is opened, said cavity is closed in said first chamber, said cavity is transferred from said first chamber to said second chamber by axial translation of said rods relative to said chambers, and said cavity is opened in said second chamber.

To open said cavity under the action of a given force and against the action of return means, when the first and second chamber are moved between two positions defined by contact of the chambers with a first and a second stop which are respectively integral with the second rod and the first rod, said rods being in contact with each other, displacement of either stop may be effected, said chambers being in contact with either stop in order to separate the ends of the rods and thus open said cavity.

The device or method may apply to sampling in a first chamber having a temperature less than minus $50°$ C. and preferably less than minus $100°$ C.

The device or method may be used for gas chromatography measurement.

BRIEF DESCRIPTION OF THE DRAWINGS

The invention will be well understood and its advantages will emerge clearly from reading the description hereinbelow of an embodiment illustrated by the attached figures wherein.

DETAILED DESCRIPTION OF A PREFERRED EMBODIMENT OF THE INVENTION

Figure 1:
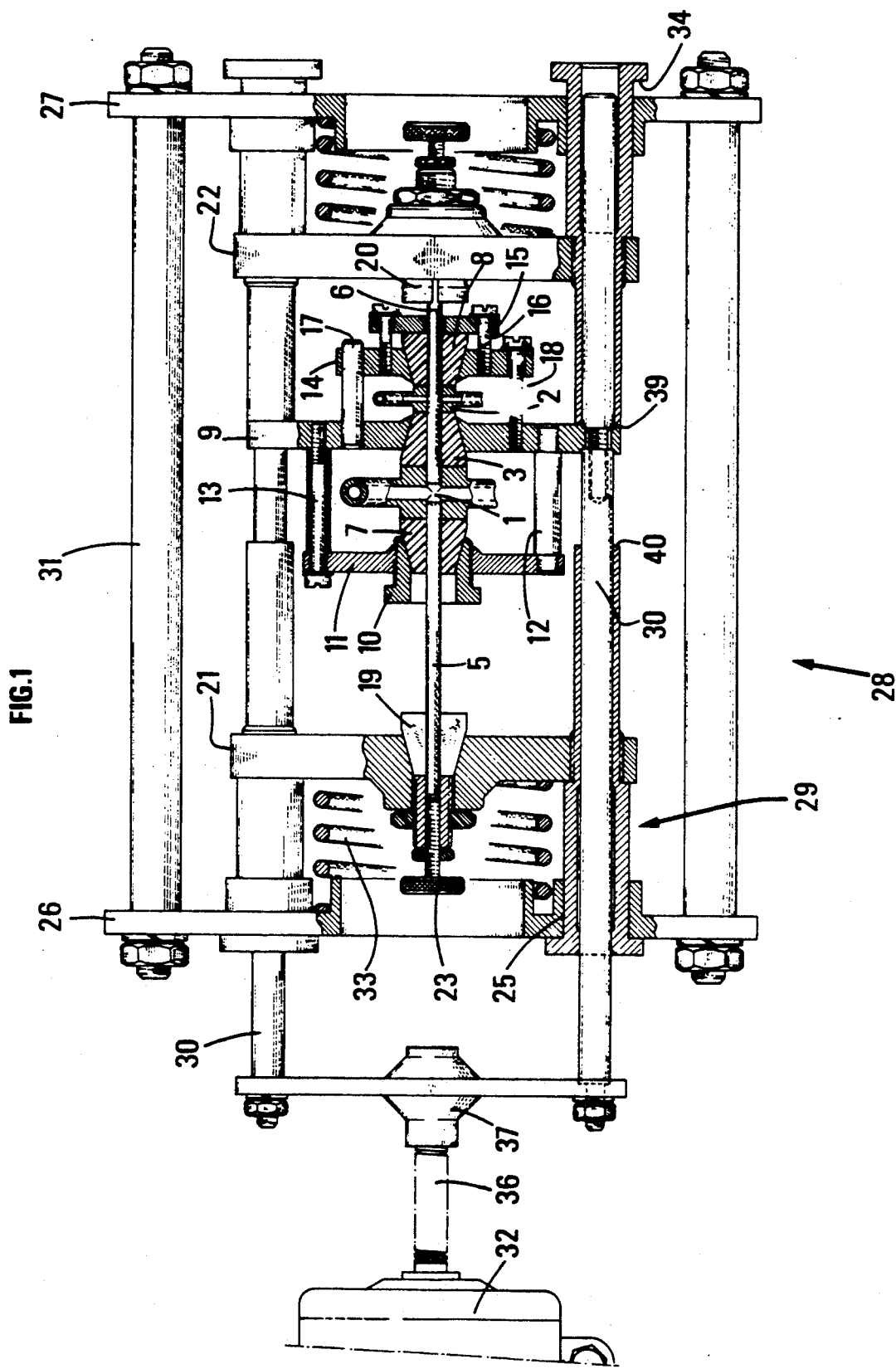
FIG. 1 shows the device according to the invention.
Figure 2:
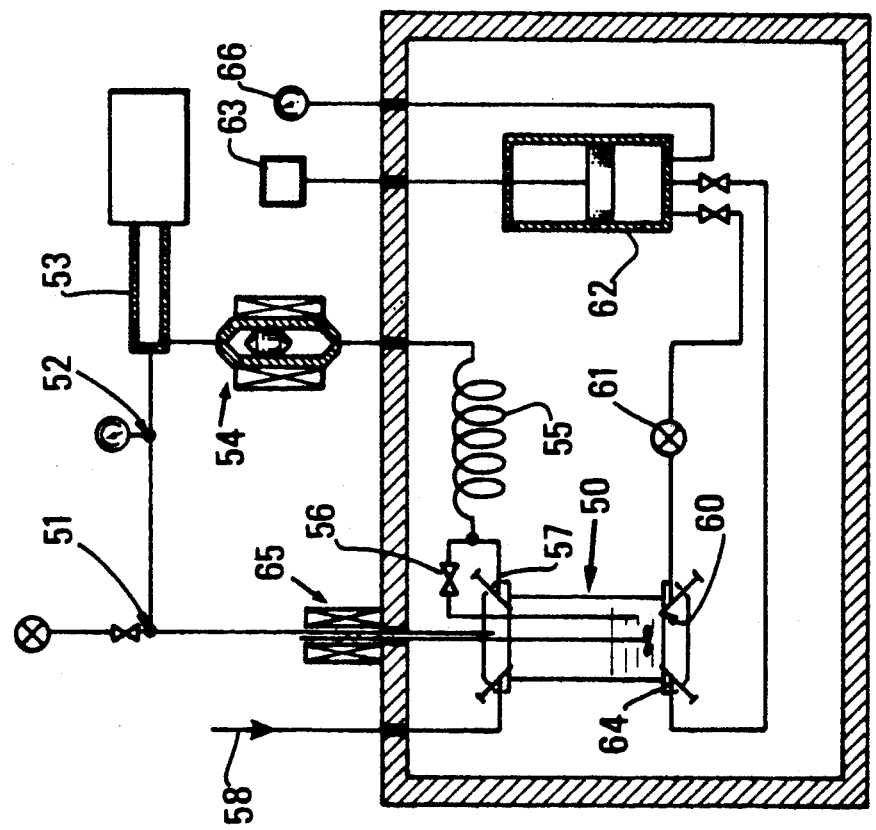
FIG. 2 shows the apparatus allowing thermodynamic measurements of a multiphase fluid mixture to be made.

FIG. 1 shows the device according to the invention which allows a fluid sample to be transferred from a first chamber 1, which communicates with the experimental apparatus shown in FIG. 2, to a second chamber 2 which communicates with a gas chromatography analysis unit.

First chamber 1 is separated from second chamber 2 by a central sealing element 3 which has an axial passage for sealing and passage of a first rod 5 and a second rod 6 having the same axis and both designed to move along this axis. First rod 5 which passes right through first chamber 1 cooperates with first lateral sealing element 7 to ensure confinement of first chamber 1 on the side of first chamber 1 opposite second chamber 2.

Second rod 6, which passes right through second chamber 2, cooperates with second lateral sealing element 8 to ensure confinement of second chamber 2 on the side of second chamber 2 opposite first chamber 1.

Depending on the positions of the first and second rods relative to said chambers, central sealing element 3 cooperates successively with first rod 5 and second rod 6 to ensure a seal between first chamber 1 and second chamber 2.

First rod 5 has, at its end, a depression-shaped area which may be closed with the end of second rod 6 when the latter is in contact with the end of first rod 5.

This depression allows fluid to be sampled in the first chamber. The volume of the cavity formed by the depression and closed off by the end of the second rod is 2 microliters.

The two chambers 1 and 2 and sealing elements 3, 7, and 8 are mounted on a chassis 9 which moves translationally relative to rods 5 and 6.

Central sealing element 3 and first lateral sealing element 7, which are both conical, are mounted such that the flared parts of the cones are in contact with the wall of first chamber 1 and the narrowest parts of these cones are directed outside the walls of first chamber 1. Central sealing element 3 is fitted into chassis 9, while the first lateral sealing element is fitted into a tapered sleeve 10 with outer threads, which cooperates with a plate 11 integral with chassis 9 to ensure tightening both of central sealing element 3 and first lateral sealing element 7 on the outer walls of first chamber 1 and on the outer walls of first rod 5 and second rod 6 at the level of central sealing element 3 and first lateral sealing element 7. Plate 11 is positioned relative to chassis 9 by means of two pins 12 and fastened to chassis 9 by means of a set of screws and spacers 13.

Second lateral sealing element 8, which is conical, is fitted into a tapered seat 14 in which the flared part of this element 8 is compressed by a stuffing-box plate 15 screwed to seat 14 by screws 16 in order to produce a seal between second rod 6 and second sealing element 8.

The narrow part of central sealing element 3 and the narrow part of lateral sealing element 8 are positioned with respect to each other by means of pins 17 and pressed against the outer walls of second chamber 2 by means of screw 18.

Sealing elements 3, 7, 8 are made of a polyimide-type polymer such as Vespel or Kinel which are trademarks of DuPont and Rhone Poulenc, respectively.

Cylindrical rods 5 and 6 which are coaxial and circular in cross section are both held identically by clamps 19, and 20 respectively, each of which has an outer conical, elastic part, an outer threaded part, and a tapped inner part.

The conical part of clamps 19 and 20 are each fitted into a conical recess of a plate 21 or 22, respectively.

A nut cooperating with plate 21 or 22, and the outer threaded part of clamps 19 or 20, tightens rods 5 and 6 in their respective clamps.

The axial positions of rods 5 or 6 relative to their clamps 19 or 20 is adjusted by a screw 23 cooperating with the inner tapped part of the clamp which provides a stop at the end of the rod, the screw being held on the clamp by a counternut.

Plates 21 and 22 are guided translationally by both shafts 30 and by bores 25 made in end-plates 26 and 27 of a frame referenced 28 as a whole which cooperates with the outer surface of four plates 29.

End-plates 26 and 27 of the frame are stiffened by stiffeners 31 and attached to a base (not shown) parallel to the plane of the figure, on which a motor 32 is also mounted.

Plates 21 and 22 are made to approach each other by expandable springs 33 which rest on plates 21 and 22 and end-plates 26 and 27 in order to ensure contact of the ends of rods 5 and 6 in the absence of spring action. The plates are held with respect to end-plates 26 and 27 by shoulders 34 of plates 29 in one translational direction.

The output shaft of motor 32 has a screw 36 which cooperates with a stop 37 which is rotationally immobile and fastened to movable shafts 30 to ensure movement of shafts 30 in one direction or the opposite direction when the motor is rotating in one direction or the opposite direction.

Displacement of shafts 30, with which chassis 9 is integral, between stops 39 and 40 of plates 29 allows the ends of rods 5 and 6, which are in contact, to be positioned at first chamber 1 or second chamber 2 and, when a particular force is applied to either stop 39 or stop 40, allows plate 22 or plate 21 respectively to be displaced, and the cavity to be opened (or the ends of the rods to be spaced) in first chamber 1 or second chamber 2, respectively. Thus, by means of displacement of shafts 30, a fluid sample can be transferred from first chamber 1, in communication with the experimental apparatus, to second chamber 2 in communication with a chromatograph.

The sampling device allows first chamber 1 to be at a very low temperature and high pressure ($-100°$ C. and 100 bars for example) and the second chamber to be at a high temperature ($150°$ C.) and a pressure of 2 bars, and a cold sample to be taken and vaporized efficiently in second chamber 2. This vaporization is sufficient to prevent condensation linked to immersion of the apparatus in a refrigerated enclosure (−100° C. for example) and insufficient to prevent cracking of the compounds of the fluid, such as hydrocarbon compounds.

FIG. 2 shows the apparatus for low-temperature thermodynamic measurements of a multiphase fluid mixture such as a mixture of hydrocarbon gases containing condensable gases.

The gas phase of the mixture above the liquid phase of the mixture in testing cell 50 flows in a closed loop forming a T with a sampling valve 51, a T 52 with a pressure gauge, a positive-displacement pump 53 which keeps the pressure of the gas and liquid phases constant, a magnetic axial circulator 54 with a linear motor, a heat exchanger 55, a T connected both to a glass tube for injection into the liquid phase, and an atomizer 57 located in the gas phase of testing cell 50. The fluid mixture is introduced into the testing cell by tube 58.

The liquid phase of the mixture is taken from cell 50 through a lower orifice 60, flows through sampling valve 61 described above and illustrated in FIG. 1 [and] a transfer cell 62 having a piston driven by a motor 63, and returns to testing cell 50 via a lower orifice 64. The liquid phase is stirred in the enclosure by a magnetic stirrer 65. The pressure in the testing cell is measured by pressure gauge 66.

Cell 50, exchanger 55, tube 56, atomizer 57, the liquid-phase sampling circuit including sampling valve 61, and transfer cell 62 are placed in a cooled enclosure. The gas-phase sampling valve mounted on T 51 is a valve of a common type. Transfer cell 62 allows the liquid phase of the mixture to be transferred from testing cell 50 through sampling valve 61.

When the liquid phase is transferred, thermodynamic equilibrium is maintained by compensating the pressure by positive-displacement pump 53. Liquid-phase sampling valve 61 is located at the same height as the bottom of cell 50 in order not to disturb the thermodynamic conditions. If valve 61 were higher relative to the bottom of cell 50, a low pressure (piezometric) would be produced, leading to selective vaporization of the components of the liquid phase which are at bubble point (equilibrium with liquid and gas phases) and incorrect sampling of the liquid phase.

Similarly, for efficient fluid transfer, the bottom of transfer cell 62 is located at the same height as the bottom of testing cell 50.

Figure 3:
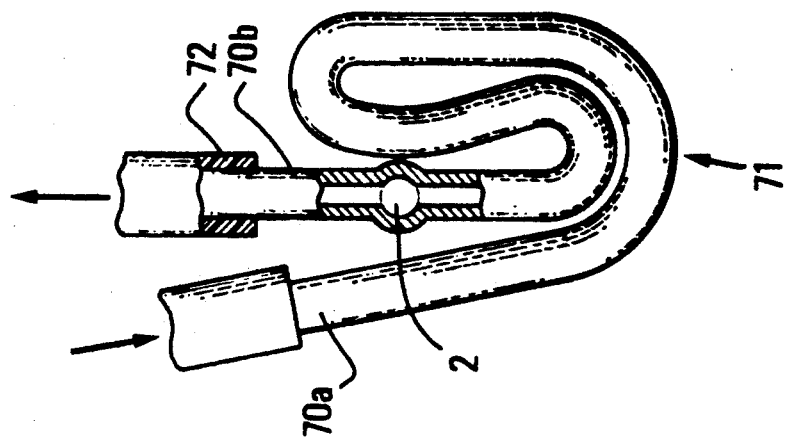
FIG. 3 is a detailed view of the second chamber showing the chromatography line with which the device according to the invention is equipped.

FIG. 3, a cross section in a plane perpendicular to the plane of FIG. 1, shows an advantageous arrangement of the chromatography line which passes through second chamber 2 of the sampling valve or transfer device shown in FIG. 1.

Line 70a, 70b with a small inside diameter, 0.5 mm for example, has an upstream part 70a through which helium is supplied and a downstream part 70b supplying a chromatography column. Upstream part 70a supplies second chamber 2 by surrounding second chamber 2 with a coil 71. Part 70b is supplied by second chamber 2.

Outside second chamber 2 and coil 71 disposed around and as near as possible to the former, line 70a, 70b of the chromatograph has heat-exchange means such as a plastic sheath 72 of the heat-shrinking type ensuring cooling of line 70a, 70b which carries helium at about 150° C. and which is heated over its entire length by the Joule effect by an alternating current provided by electrical means, not shown.

Contrary to what would appear obvious, the heat-shrinking plastic used, of an electric type, does not heat-insulate the pipe, but increases its heat exchange.

Plastic sheath 72 used is 0.4 mm thick and has a heat transfer coefficient $\lambda$ of 4W/m.K. For this material, the accentuated heat-exchange effect is felt up to a sheath thickness of 2.5 mm.

By this arrangement of line 70a, 70b and chamber 2, on the one hand, marked local heating of chamber 2 and the gas near the chamber is obtained, which allows correct vaporization of the fluid sample taken, and on the other hand, in part 70a of the line, both overheating and condensation of the compounds of the sample taken are avoided.

In this way, the temperature of the fluid flowing in line 70a could be increased or its temperature at the inlet to this line 70a could be decreased by not covering it with heat-shrinking plastic.

Overheating may cause cracking of certain components of the fluid such as hydrocarbon components.

In order to heat the second chamber of the device according to the invention by electrical means only, the second rod is made of a ceramic of the Zircone type which is an electrical insulator and whose slippage with lateral sealing element 8 and central sealing element 3 is satisfactory.

The end of first rod 5 which is $2.5_{-0.006}{}^{-0}$ mm and which is made of stainless steel, forms a depression in the shape of a 90° cone, open on the side of the rod end, and whose base is $2_{-0.2}{}^{-0}$ m [sic] in diameter.

The annular space between the base of the cone and the diameter of first rod 5 is a plane surface perpendicular to the shaft of first rod 5.

The end of second rod 6 which also has an outside diameter of $2.5_{-0.006}{}^{-0}$ mm is a plane surface perpendicular to the shaft of the second rod.

The angle between the plane annular surface of the first rod or the plane surface of the end of the second rod and the outer cylindrical wall of the first or second rod is a right angle (not broken).

The depression could also have been made in the shape of a cone in the second rod, or the cavity located at the ends of the rods could be made by generating a shape at each of the ends of the rods.

We claim:

1. A device for transferring a fluid sample from a first chamber to a second chamber, separated from the first chamber, said device comprising a first rod and a second rod, each rod having a lengthwise axis, the lengthwise axis of each rod being arranged coaxially with the other, an outer cylindrical wall of the first rod and an outer cylindrical wall of the second rod each being arranged to cooperate with a central circumferential sealing element in order to provide a seal between the first chamber and the second chamber, said rods being displaceable coaxially in a direction along a common axis relative to said chambers and relative to each other, at least said first rod having an end portion, which has an open cavity formed therein, said end portion being arranged to cooperate with an end portion of the second rod to close said cavity when the end portions contact each other, the first rod and the second rod each having outer cylindrical walls with the same dimensions, displacement means for moving the two rods together to form the closed cavity and to move the closed cavity between the first chamber and the second chamber, means for opening said closed cavity in said first chamber or in said second chamber, respectively, and means for closing the open cavity when a sample is to be transferred from the first chamber to the second chamber via said closed cavity.

2. A device according to claim 1, wherein the first rod and the second rod pass through said first chamber and the second chamber, respectively, and cooperate with a first lateral sealing element or a second lateral sealing element, respectively, ensuring confinement of the first chamber or second chamber, respectively.

3. A device according to claim 1 or claim 2, wherein the second chamber communicates with an analysis device.

4. A device according to claim 3, wherein the second chamber comprises a portion of a sampling line to which a carrier gas flows.

5. A device according to claim 1, further comprising means for heating at least one of said chambers, a heated chamber being a portion of electrically conductive line through which a fluid flows, the device further comprising electrical means for causing a current to flow in said line to produce heating of said line by the Joule effect and the central sealing element and one of said rods located in said heating chamber being electrically resistive.

6. A device according to claim 1, further comprising means for allowing at least one of said chambers to be cooled or heated and kept at a given temperature, said at least one of said chambers being a portion of line in which a cooling or heating fluid flows, said line having a coil arranged around said at least one of said chambers, so that circulation of the fluid cools or heats said at least one of said chambers, respectively.

7. A device according to claim 5, wherein said line has at least outside one of said chambers, a heat exchange means outside of said line designed for transferring heat energy between said line and a medium external to said line.

8. A device according to claim 7, wherein said line having a coil is arranged around said chamber to be heated or cooled and a heat exchange means is disposed on said line outside of said coil.

9. A device according to claim 2, wherein at least one of said sealing elements is made of a polymer material comprising a polyimide.

10. A device according to claim 1, wherein said first rod and said second rod pass through the first chamber and the second chamber, respectively, and cooperate with a first lateral sealing element and a second lateral sealing element, respectively, for ensuring confinement of the first chamber and the second chamber, respectively, said device further comprising a shaft operatively associated with said first chamber and said second chamber, with a central sealing element, with the first lateral sealing element and the second lateral sealing element, a first stop and a second stop which are operatively associated with the first rod and the second rod, respectively, said shaft moving relative to said rods between said stops in order to place the end portions of the first rod and the second rod in the first chamber when the shaft is in contact with the first stop and in the second chamber when the shaft is in contact with the second stop and said means for opening said closed cavity having elastic elements for allowing first the stops to move under the action of a given force produced by said shaft in order to cause the cavity to open and said means for closing said cavity allowing replacement of the stops when said given force is removed in order to cause closure of said cavity, the end portions of the first rod and of the second rod then being in contact with each other.

11. A device according to claim 1, wherein the first rod or the second rod is made of a ceramic material.

12. A method for transferring a fluid sample from a first chamber to a second chamber separated from the first chamber which comprises the following steps:
opening a closed cavity defined between end portions of two coaxially arranged cylindrical rods, said rods having cylindrical walls of the same dimensions;
closing the cavity opened in said first chamber;
transferring a closed cavity from the first chamber to the second chamber by axial movement of said rods, relative to said chambers; and
opening the closed cavity in said second chamber; a sample trapped in the first chamber during closing of the open cavity being transferred via the closed cavity to said second chamber upon opening of the closed cavity in the second chamber.

13. A method according to claim 12, wherein said first chamber and said second chamber are moved between two positions defined by contact of a chassis integral with the chambers, with a first stop and a second stop, respectively, operatively associated with a second rod and a first rod, respectively, said rods being in contact with each other to form said closed cavity; and in order to open said closed cavity under an action of a given force and against the action of a return means effecting displacement of one or the other of the stops, said chassis being in contact with one or the other of the two stops in order to separate the end portions of the rods and thus to open said closed cavity.

14. A method according to claim 12, wherein a fluid sample is taken from the first chamber having a temperature less than $-50°$ C. and transferred to the second chamber at a different temperature.

15. A method according to claim 14, wherein the fluid sample is subjected to a gas chromatography measurement after being removed from the second chamber.

* * * * *